United States Patent [19]

Hurtel et al.

[11] Patent Number: 4,857,239

[45] Date of Patent: Aug. 15, 1989

[54] PROCESS FOR THE SYNTHESIS OF (METH)ACRYLIC ANHYDRIDES

[75] Inventors: Patrice Hurtel; Denis Laurent, both of Saint Avold; Joseph Rondini, Ham Sous Varsberg, all of France

[73] Assignee: Norsolor, Paris Defense, France

[21] Appl. No.: 188,585

[22] Filed: Apr. 29, 1988

Related U.S. Application Data

[63] Continuation of Ser. No. 945,989, Dec. 24, 1986, abandoned.

[30] Foreign Application Priority Data

Dec. 24, 1985 [FR] France .................................. 85 19116

[51] Int. Cl.$^4$ ............................................. C07C 57/04
[52] U.S. Cl. .................................................... 562/896
[58] Field of Search .......................................... 260/546

[56] References Cited

U.S. PATENT DOCUMENTS 2,319,070  5/1943  Lowe et al. .......................... 260/546
2,411,567 11/1946  Fisher et al. ......................... 260/413

FOREIGN PATENT DOCUMENTS

EP4-641  10/1979  European Pat. Off. .
0170964   2/1985  European Pat. Off. .
  53810   7/1941  United Kingdom .
3037301   6/1982  United Kingdom .

Primary Examiner—Paul J. Killos
Attorney, Agent, or Firm—Millen, White & Zelano

[57] ABSTRACT

The present invention relates to a process for the synthesis of (meth)acrylic anhydride, according to which (meth)acrylic acid is reacted with acetic anhydride in the presence of at least one polymerization inhibitor, in a reactor surmounted by a distillation column. This process is characterized in that the mole ratio of (meth)acrylic acid to acetic anhydride is chosen to be between 2 and 5, in that the reaction is performed in the absence of catalyst, and in that:

the acetic acid formed during the reaction is drawn off, and at least one polymerization inhibitor is gradually introduced into the top of the distillation column during the reaction and the distillation enabling the (meth)acrylic anhydride formed to be separated.

The (meth)acrylic anhydrides thereby obtained are used, in particular, as reagents in the preparation of (meth)acrylates.

9 Claims, No Drawings

PROCESS FOR THE SYNTHESIS OF (METH)ACRYLIC ANHYDRIDES

This application is a continuation of applic. Ser. No. 945989 filed Dec. 24, 1986, now abandoned.

The present invention relates to a new process for the synthesis of (meth)acrylic anhydrides. By (meth)acrylic anhydrides, there is understood methacrylic anhydride or acrylic anhydride.

A process for the synthesis of (meth)acrylic anhydrides is currently known, according to which (meth)acrylic acid is reacted with acetic anhydride in the presence of a catalyst, for example a strong acid such as sulphuric acid or alternatively zinc chloride. The main problem arising in the above-recited process, which is a considerable problem, resides in the formation of an impurity which promotes the polymerization of the reaction medium. Analyses have shown that this impurity is mainly composed of cyclic dimer of (meth)acrylic acid. Pursuing these investigations further, the Applicant has developed a new process for the synthesis of (meth)acrylic anhydrides, according to which, surprisingly, in the absence of catalyst, excellent yields of (meth)acrylic anhydrides are obtained with a considerable reduction in the formation of the troublesome impurity.

More specifically, the process according to the invention consists in reacting (meth)acrylic acid with acetic anhydride in the presence of at least one polymerization inhibitor, in a reactor surmounted by a distillation column. This process is characterized in that the mole ratio of (meth)acrylic acid to acetic anhydride is chosen to be between 2.05 and 5, in that the reaction is performed in the absence of catalyst, and in that:

- the acetic acid formed during the reaction is drawn off, and
- at least one polymerization inhibitor is gradually introduced into the top of the distillation column during the reaction and the distillation enabling the (meth)acrylic anhydride formed to be separated.

Advantageously, the polymerization inhibitor introduced at the column head is diluted in an organic solvent. Preferably, during the reaction it is diluted in acetic acid, and during the distillation it is diluted in (meth)acrylic anhydride.

The reaction temperature is maintained at between 60° and 170° C., and preferably between 60° and 80° C.

The pressure during the reaction is maintained at between atmospheric pressure and 10 mmHg, and preferably between 100 and 5U mmHg.

According to a preferred embodiment of the process according to the invention, with the object of facilitating the operation of drawing off the acetic acid and hence the formation of (meth)acrylic anhydrides, the reaction temperature is maintained constant and the pressure is decreased by a difference value generally of between 10 and 50 mmHg during the reaction, or, in a different manner, the pressure is maintained constant and the reaction temperature is increased by a difference value generally of between 5° and 20° C.

The mole ratio of (meth)acrylic acid to acetic anhydride is preferably chosen to be between 2.1 and 3.

The (meth)acrylic acids to which the present invention relates are acrylic acid and methacrylic acid.

Among the polymerization inhibitors, it is possible to use phenothiazine, methylene blue, iron sulphate, a copper salt such as copper acetate or copper sulphate, or a mixture of these inhibitors. In the reactor, at least 1,000 ppm of polymerization inhibitor are generally used. In the top of the distillation column at least 250 ppm of polymerization inhibitor are gradually introduced.

The process according to the invention makes it possible to achieve high yields, and most often greater than 80% and of the order of 90-95%.

In addition, the process according to the invention enables the formation of (meth)acrylic acetate mixed anhydride to be avoided.

(Meth)acrylic anhydrides are used, in particular, as reagents in the synthesis of (meth)acrylamides such as dimethylaminopropyl(meth)acrylamide, or alternatively in the synthesis of (meth)acrylates, for example fluorinated (meth)acrylates such as trifluoroethyl (meth)acrylate.

The examples given below as a guide will enable the invention to be better understood.

EXAMPLE 1

Synthesis of methacrylic anhydride

The following charge (in parts by weight) is introduced into a reactor equipped with a mechanical stirring system, electrically heated and surmounted by a distillation column:

| | |
|---|---|
| methacrylic acid | 537 |
| acetic anhydride | 255 |
| phenothiazine | 2,000 ppm |
| methylene blue | 2,000 ppm |

The reaction mixture is subjected to stirring at a temperature which rises from 70° to 80° C. during the reaction and, throughout the reaction which lasts for 3 h 15 min., the acetic acid is drawn off. The pressure is 100 mmHg at the beginning of the reaction and 50 mmHg at the end of the reaction. In addition, during the reaction and the distillation, 250 ppm of methylene blue are gradually introduced at the column head. After the reaction, distillation is performed. There are distilled, as the first fraction, unreacted methacrylic acid and acetic anhydride and a little methacrylic anhydride from 50° to 107° C. under 35 mmHg. This fraction represents 177 parts by weight. The methacrylic anhydride is then distilled at 108° C. under 35 mmHg. 335 parts by weight of methacrylic anhydride are collected.

The reaction yield is 95%.

EXAMPLE 2

Synthesis of acrylic anhydride

The following charge (in parts by weight) is introduced into an assembly identical to that described in Example 1:

| | |
|---|---|
| acrylic acid | 540 |
| acetic anhydride | 306 |
| copper sulphate | 2,000 ppm |
| phenothiazine | 2,000 ppm |

The reaction mixture is subjected to stirring and, throughout the reaction which lasts for 4 hours, the acetic acid is drawn off under a pressure of 100 mmHg, the temperature being 75° C. at the beginning of the reaction and 85° C. at the end of the reaction. In addition, during the reaction and during the distillation, 500 ppm of copper sulphate and 500 ppm of phenothiazine are gradually introduced into the top of the distillation column. After the reaction, distillation is performed. There are distilled, as the first fraction, unreacted acetic anhydride and acrylic acid as well as a little acrylic anhydride under 20 mmHg at a temperature which is varied between 58° and 74° C. This fraction represents 183 parts by weight. The acrylic anhydride is then distilled at 80° C. under 25 mmHg. 302 parts by weight of acrylic anhydride are collected.

The yield is 95%.

COMPARATIVE EXAMPLE 3

Synthesis of acrylic anhydride

The following charge (in parts by weight) is introduced into an assembly identical to that described in Example 1:

| | |
|---|---|
| acrylic acid | 432 |
| acetic anhydride | 408 |
| copper sulphate | 2,000 ppm |
| phenothiazine | 2,000 ppm |

In this example, the mole ratio between acrylic acid and acetic anhydride is equal to 1.5. The reaction mixture is subjected to stirring and, throughout the reaction which lasts for 5 hours, the acetic acid is drawn off under a pressure of 100 mmHg, the temperature being 85° C. at the beginning of the reaction and 95° C. at the end of the reaction. In addition, during the reaction and during the distillation, 500 ppm of copper sulphate and 500 ppm of phenothiazine are gradually introduced into the top of the distillation column. After the reaction, distillation is performed. There are distilled, as a first fraction, unreacted acetic anhydride and acrylic acid, acrylic acetic mixed anhydride as well as a little acrylic anhydride, under 200 mmHg at a temperature of 57° to 76° C. under 20 mmHg. This fraction represents 140 parts by weight. The acrylic anhydride is then distilled at 76° C. under 20 mmHg. 250 parts by weight of acrylic anhydride are collected. The yield is 75%.

Example 4 (comparative)

Synthesis of acrylic anhydride

If the procedure is performed according to Example 1, without stabilizing the top of the distillation column, a polymerization of the acrylic monomers is observed, this occurring both in the reactor and in the column.

We claim:

1. Process for the synthesis of (meth)acrylic anhydrides according to which (meth)acrylic acid is reacted with acetic anhydride in the presence of at least one polymerization inhibitor, in a reactor surmounted by a distillation column, the process being characterized in that the mole ratio of (meth)acrylic acid to acetic anhydride is chosen to be between 2.05 and 5, in that the reaction is performed in the absence of catalyst, and in that:
   the acetic acid formed during the reaction is drawn off, and
   at least one polymerization inhibitor is gradually introduced into the top of the distillation column during the reaction and the distillation enabling the (meth)acrylic anhydride formed to be separated.

2. Process according to claim 1, characterized in that the reaction temperature is maintained at between 60° and 170° C.

3. Process according to claim 2, characterized in that the reaction temperature is maintained at between 60° and 80° C.

4. Process according to claim 1, characterized in that the pressure during the reaction is maintained at between atmospheric pressure and 10 mmHg.

5. Process according to claim 4, characterized in that the pressure is maintained at between 10 and 50 mmHg.

6. Process according to claim 1, characterized in that, during the reaction, the temperature is maintained constant and the pressure is decreased by a difference value of between 10 and 50 mmHg.

7. Process according to claim 1, characterized in that, during the reaction, the pressure is maintained constant and the temperature is increased by a difference value of between 5° and 20° C.

8. Process according to claim 1, characterized in that the mole ratio of (meth)acrylic acid to acetic anhydride is between 2.1 and 3.

9. Process according to claim 1, characterized in that the quantity of polymerization inhibitor used is at least 1,000 ppm in the reaction and at least 250 ppm in the top of the distillation column.

* * * * *

UNITED STATES PATENT AND TRADEMARK OFFICE
CERTIFICATE OF CORRECTION

PATENT NO. : 4,857,239
DATED : AUGUST 15, 1989
INVENTOR(S) : HURTEL ET AL

It is certified that error appears in the above-identified patent and that said Letters Patent is hereby corrected as shown below:

Title page, title: reads "PROCESS FOR THE SYNTHESIS OF (MATH)ACRYLIC ANHYDRIDES"

should read -- PROCESS FOR THE SYNTHESIS OF (METH)ACRYLIC ANHYDRIDES --

Signed and Sealed this

Twelfth Day of June, 1990

Attest:

HARRY F. MANBECK, JR.

*Attesting Officer*  *Commissioner of Patents and Trademarks*